United States Patent [19]
Kerrigan et al.

[11] Patent Number: 5,304,721
[45] Date of Patent: Apr. 19, 1994

[54] **METHOD FOR THE PRODUCTION OF HIGH PROPORTIONS OF HOMOKARYONS IN BREEDING STOCK OF THE MUSHROOM *AGARICUS BISPORUS***

[75] Inventors: Richard W. Kerrigan, Worthington; Mark C. Spear, Cabot, both of Pa.

[73] Assignee: Sylvan Spawn Laboratory Incorporated, Kittanning, Pa.

[21] Appl. No.: 900,546

[22] Filed: Jun. 18, 1992

[51] Int. Cl.$^5$ .................. A01H 15/00; A01H 1/00; A01G 1/04
[52] U.S. Cl. .................. 800/200; 800/DIG. 8; 47/1.1; 47/58
[58] Field of Search .................. 800/200, DIG. 8; 47/1.1, 1.102, 58.03

[56] References Cited

PUBLICATIONS

Wallace et al (1981) Biology: Science of Life Scott Foresman and Co., Dallas, Tex.
Sass, J. E., 1929. "A Cytological Study of a Bispored Form of *Psalliota campestris*." Pap., Mich Acad. Sci. 9: 287-298.
Bretzloff, C. W., W. A. Robbins, and J. H. Curme, 1962. "Observations on Multisporous Isolates From the Cultivated Mushroom *Agaricus bisporus* (Lange) Sing." Mush. Sci. 5: 188-196.
Moessner, E. J., 1962. "Preliminary Studies of the Possibility of Obtaining Improved Cultures Through Mycelial Fusion (Anastomoses)." Mush. Sci. 5: 197-203.
Pelham, J., 1965. "Techniques for Mushroom Genetics." Mush. Sci. 6: 49-64.
Miller, R. E., 1971. "Evidence of Sexuality in the Cultivated Mushroom, *Agaricus bisporus*." Mycologia 63: 630-634.
Miller, R. E., and D. L. Kananen, 1972. "Bipolar Sexuality in the Mushroom." Mush. Sci. 8: 713-718.
Elliott, T.J., 1972. "Sex and the Single Spore." Mush. Sci. 8: 11-18.
Kneebone, L. R., P. G. Shultz, and T. G. Patton, 1972. "Strain Selection and Development by Means of Mycelial Anastomosis." Mush. Sci. 8: 19-25.
Raper, C. A., J. R. Raper, and R. E. Miller, 1972. "Genetic Analysis of the Life Cycle of *Agaricus bisporus*." Mycologia 64: 1088-1117.
Peng, J.-T., and K.-J. Hu, 1974. "Cultivation of Vegetative Segregants derived from a Monosporous Culture of Cultivated Mushroom, *Agaricus bisporus*." Mush. Sci. 9: 31-37.
Stubnya, K., 1978. "Producing New Strains of *Agaricus bisporus*." Mush. Sci. 10: 83-89.
Stalpers, J. A., and A. van Zaayen, 1981. "Scanning Electron Microscopy of Basidiospores of *Agaricus bitorquis* and of Healthy and Virus-infected *Agaricus bisporus*." Mush. Sci. 11: 449-454.
Royse, D. J., and B. May, 1982. "Use of Isozyme Variation to Identify Genotypic Classes of *Agaricus brunnescens*." Mycologia 74: 93-102.
Spear, M. C., D. J. Royse, and B. May, 1983. "Atypical Meiosis and Joint Segretation of Biochemical Loci in *Agaricus brunnescens*." J. Heredity. 74: 417-420.
Elliott, T. J., and M. P. Challen, 1984. "Effect of Temperature on Spore Number in the Cultivated Mushroom *Agaricus bisporus*." Trans. Br. Mycol. Soc. 82: 293-296.
Kerrigan, R. W., and I. K. Ross, 1987. "Dynamic Aspects of Basidiospore Number in Agaricus." Mycologia 79: 204-215.
Kerrigan, R. W., and I. K. Ross, 1986. "Basidiospore Number Variation in Agaricus." Proc. Intl. Symp. Sci.

(List continued on next page.)

Primary Examiner—David T. Fox
Assistant Examiner—E. F. McElwain
Attorney, Agent, or Firm—Renner, Kenner, Greive, Bobak, Taylor & Weber

[57] ABSTRACT

A method for the production of high proportions of homokaryons among spores from breeding stock of the mushroom *Agaricus bisporus* includes the steps of providing a first strain of *Agaricus bisporus* carrying a gene or genes which determines the trait for production of basidia which predominantly bear at least three spores rather than two, and crossing the first strain of *Agaricus bisporus* with a second, different strain of *Agaricus bisporus*.

46 Claims, No Drawings

OTHER PUBLICATIONS

Tech. Aspects Cult. Edible Fung., pp. 155–162.

May, G., 1988. "Somatic Incompatibility and Individualism in the *Coprophilous basidiomycete, Coprinus cinereus.*" Trans. Br. Mycol. Soc. 91: 443–451.

Kerrigan, R. W., and I. K. Ross, 1989. "Allozymes of a Wild *Agaricus bisporus* Population: New Alleles, New Genotypes." Mycologia 81: 433–443.

Wilson, A. D., 1991, "Somatic Incompatibiliuty in Dikaryotic–monokaryotic and dikaryotic Pairings of *Echinodontium tinctorium.*" Can. J. Bot. 69: 2716–2723.

Kerrigan, R. W., L. M. Baller, P. A. Horgen, and J. B. Anderson, 1991. "Strategies for the Efficient Recovery of *Agaricus bisporus* Homokaryons." Mycologia (In press: Jul.–Aug. 1992).

Kerrigan, R. W., P. A. Horgen, and J. B. Anderson, 1993. "The California Population of *Agaricus bisporus* Comprises at Least Two Ancestral Elements." Syst. Bot. (In press: Jan. 1993).

Lange, M., 1959. "The Two–Spored Basidium". Mush. Sci. 4: 30–32.

Song, S. F., K. J. Hu, and Y. L. Hsieh, 1972. "Observations on the Spored–Basidium in the Cultivated Mushrooms in the Cultivated Mushrooms (*Agaricus bisporus*)". Mush. Sci. 7: 295–303.

Elliott, T. J., 1977. "Basidiospore Numbers in *Agaricus bisporus* (Lange) Imbach". J. Bacteriol. 192: 525–526.

Castle, A. J., P. A. Horgen, and J. B. Anderrson, 1987. "Restriction Fragment Length Polymorphisms in the Mushroom *Agaricus brunnescens* and *Agaricus bitorquis*". Appl Env. Microbiol. 53: 816–822.

Sonnenberg, A. S., J. G. Wessels, and L. J. van Griensven, 1988. "An Efficient Protoplasting/Regeneration System for *Agaricus bisporus* and *Agaricus bitorquis*". Curr. Microbiol. 17: 285–291.

Royse, D. J. and B. May, 1989. "Identification and Use of Three New Biochemical Markers in *Agaricus bisporus*". Agric. Biol. Chem. 53: 2861–2866.

Wang, Z. S., J. H. Liao, F. G. Li and H. C. Wang, 1991. "Studies on genetic basis of esterase isozyme loci Est A, B, and C in *Agaricus bisporus*". pp. 3–9 in Maher, M. J., Ed. *Science and Cultivation of Edible Fungi, vol. 1.* A. A. Balkema, Rotterdam.

Lambert, E. B., 1929, "The Production of Normal Sporophores in Monosporous Cultures of *Agaricus campestris*", Mycologia 21:333–335.

Whitehouse, H. L. K., 1949, "Multiple-Allelomorph Heterothallism in the Fungi", Botany School, University of Cambridge, New Phytol 48:212–244.

Lange, M., 1952, "Species Concept in the Genus Corprinus—A Study on the Significance of Intersterility", Dansk Botanisk Arkiv Copenhagen, Ejnar Munksgaard.

Burnett, J. H. and Boulter, M. E., 1963, "The Mating Systems of Fungi—II. Mating Systems of the Gasteromycetes Mycocalia Denudata and M. Duriaeana", The Department of Botany, King's College, Newcastle upon Tyne I, New Phytol 62:217–236.

Macrae, R., 1967, "Pairing Incompatibility and Other Distinctions Amoung Hirschioporus [Polyporus] Abietinus, H. Fusco-Violaceus, and H. Laricinus", Canadian Journal of Botany, vol. 45.

Petersen, R. H. (ed.), 1971, Boidin. J., "Nuclear Behavior in the Mycelium and the Evolution of the Basidiomycetes", The University of Tennessee Press, Knoxville.

Ullrich, R. C., 1973, "Sexuality, Incompatibility, and Intersterility in the Biology of the Sistotrema Brinkmannii Aggregate", Mycologia, vol. LXV, No. 6, pp. 1234–1249.

Miller, R. E. Robbins, W. A. and Kananen, D. L., 1974, "Inheritance of Sporophore Color and 'Wild' Morphology in *Agaricus bisporus*", Mush., Sci. IX (Part I).

Elliott, T. J., 1978, "Comparative Sexuality in Agaricus Species", Journal of General Microbiology, 107, 113–122.

Anderson, J. B. and Ullrich, R. C., 1979, "Biologocal Species of Amillaria Mellea in North America", Mycologia, Vol. LXXI, No. 2, pp. 402–414.

Kemp, R. F. O., 1980, "Genetics of A–B–C Type Heterokaryon Incompatibility in Corpus Bisporus", Br. mycol. Soc. 75(1) 29–35.

Hallenberg, N., 1983, "Hericium Coralloides and H. Alpestre (Basidiomycetes)", Mycotaxon, vol. XVIII, No. 1, pp. 181–189.

Kerrigan, R. W., 1986, "The Agaricales (Gilled Fungi) of California—6. Agaricaceae", Mad River Press, Inc., Eureka, California.

Vilgalys, R. and Miller, O. K., Jr., 1987, "Mating Relationships Within the Collybia Dryophila Group in Europe", Trans. Br. Mycol. Soc. 89(3), 295–300.

Bresinsky, A., Fischer, M., Meixner, B. and Paulus, W., 1987, "Speciation in Pleurotus", 79(22), pp. 234–245.

Chase, T. E. and Ullrich, R. C., 1990, "Five Genes Determining Intersterility in Heterobasidion Annosum"; Mycologia, 82(1), pp. 73–81.

METHOD FOR THE PRODUCTION OF HIGH PROPORTIONS OF HOMOKARYONS IN BREEDING STOCK OF THE MUSHROOM *AGARICUS BISPORUS*

TECHNICAL FIELD

This invention relates to the production and improvement of mushrooms, the sporocarps of edible agaric fungi. More particularly, this invention relates to a method for producing high proportions of homokaryons in breeding stocks of the mushroom species *Agaricus bisporus* (Lange) Imbach, strains of which may be commercially cultivated. Specifically, this invention relates to the introduction of the heritable four-spored trait into stocks of *Agaricus bisporus* mushrooms, by producing hybrid *Agaricus bisporus* mushrooms which carry and express the trait and which produce large percentages or fractions of homokaryons which may be easily recovered from among the offspring of the hybrid.

BACKGROUND OF THE INVENTION

The mushroom species *Agaricus bisporus* (Lange) Imbach, also known as *Agaricus brunnescens* Peck, is a well known and widely cultivated commercial mushroom. At least one distinct variety of this species of mushroom has been the subject of a U.S. Plant Pat. No. 7,636, incorporated herein by reference.

Notably, a distinctive characteristic of *Agaricus bisporus*, that historically has defined the species, is that virtually all known strains predominantly produce only two spores on each basidium. Small percentages of aberrant basidia having as many as eight spores and as few as one spore have been shown to occur in various *Agaricus bisporus* strains. Nevertheless, following meiosis in a typical two-spored basidium of *Agaricus bisporus*, each spore receives two nuclei which are jointly necessary for fertility. As a result, most spores for this species of mushroom produce fertile, heterokaryotic progeny. This two-spored trait characterizes all commercially cultivated strains as well as the great majority of naturally occurring or "wild" strains of *Agaricus bisporus* thus far discovered. Such a trait of self-fertility poses a problem for the mushroom breeder because heterokaryons undergo little, if any, hybridization.

In contrast, all other known species of Agaricus produce predominantly four-spored basidia. In agaric fungi, the four-spored trait is associated with the production of mononucleate homokaryotic spores which are not fertile. In mushroom breeding, homokaryons, haploid strains which function in a manner similar to the gametes of plants and animals, are generally required for the practical crossbreeding of stocks to produce new hybrid strains. Homokaryons mate easily with other compatible homokaryons. However, although rare, it is possible to cross a homokaryon and a heterokayron or, in even rarer instances, to cross two heterokaryons.

To produce hybrids, homokaryons from the parent varieties of mushrooms must fuse and establish a common heterokaryotic cytoplasm. However, homokaryons are presently very difficult to obtain by conventional spore isolation from the two-spored *Agaricus bisporus* strains because less than three percent of the spores typically produced by such strains are homokaryotic. The great majority of spores of these strains produce fertile, heterokaryotic progeny as noted hereinabove.

Moreover, heterokaryotic and homokaryotic offspring are generally indistinguishable from one another except by genetic screening, such as by the use of allozyme or DNA markers, which is time consuming and costly. Homokaryons are also difficult to obtain by other presently available methods. For a more complete description of some conventional methodologies for the recovery of *Agaricus bisporus* homokaryons, and some difficulties and drawbacks thereof, see "Strategies For The Efficient Recovery of *Agaricus bisporus* Homokaryons" by Kerrigan et al. in *Mycologia,* 84(4), 575–579 (1992), hereby incorporated by reference.

Therefore, the need exists for a process which will permit the mushroom breeder to obtain large percentages and fractions of homokaryons relatively quickly, efficiently and inexpensively from the breeding stock of the *Agaricus bisporus* mushroom.

SUMMARY OF INVENTION

It is, therefore, an object of the present invention to provide a method for producing homokaryons from the breeding stock of the cultivated mushroom species *Agaricus bisporus*.

It is another object of the present invention to provide a method, as above, which is less costly and time consuming than the present methods for producing and screening for homokaryons from breeding stocks of this particular species of mushroom.

It is still another object of the present invention to provide a method, as above, which would eliminate the necessity of genetic screening for identification of homokaryons of *Agaricus bisporus*.

It is yet another object of the present invention to provide a method, as above, which will produce a large percentage or fraction of homokaryons of *Agaricus bisporus*.

It is still a further object of the present invention to provide a method for introducing the four-spored trait into two-spored stocks of *Agaricus bisporus*.

These and other objects of the present invention, together with the advantages thereof over known methods, which shall become apparent from the description which follows, are accomplished by the invention as hereinafter described and claimed.

In general, the present invention provides a method for the production of homokaryons from breeding stock of the mushroom *Agaricus bisporus* which includes the steps of providing a first strain of *Agaricus bisporus* carrying at least one gene which determines the trait for production of basidia which predominantly bear at least three spores, and crossing the first strain with at least a second strain of *Agaricus bisporus*.

The present invention also provides a method for introducing a trait for the production of basidia which predominantly bear at least three spores into breeding stock of mushroom *Agaricus bisporus* which includes the steps of providing a first strain of *Agaricus bisporus* carrying at least one gene which determines the trait for production of basidia which predominantly bear at least three spores, and incorporating the gene or genes into the genetic background of at least a second strain of *Agaricus bisporus*.

The present invention also provides for homokaryons produced from hybrid mushrooms and their descendants formed by providing a first strain of *Agaricus bisporus* carrying at least one gene which determines the trait for production of basidia which predominantly bear at least three spores; and crossing the first strain with at least a second strain of *Agaricus bisporus*.

PREFERRED EMBODIMENT FOR CARRYING OUT THE INVENTION

The production of homokaryotic offspring from both wild and cultivated, two-spored breeding stock of the commercial mushroom *Agaricus bisporus* has always been time consuming and costly. Although small percentages of basidia of *Agaricus bisporus* have been shown to have as many as eight spores and as few as one spore, this species of mushroom characteristically predominantly produces two-spored basidia rather than predominantly four-spored basidia like all other known Agaricus. Thus, the resultant offspring from the spores are mostly, and sometimes always, heterokaryotic. Consequently, much effort and expense is associated with testing, either genetically or otherwise, to determine which of the spores of each mushroom are homokaryotic and which are heterokaryotic. For example, research experience indicates that, on average, it generally takes a researcher one or two days of effort to obtain a single homokaryon using conventional random spore isolation methods. Even greater effort and expense may be associated with obtaining homokaryons by alternative means such as microsurgery or protoplast production.

The present invention provides a novel method for obtaining homokaryons from the strains of *Agaricus bisporus* in much greater proportions than they are currently found. For example, it is believed that more homokaryons could be obtained in one day in one laboratory by using the present invention than have been obtained worldwide since efforts to isolate *Agaricus bisporus* homokaryons began circa twenty-five years ago. This method is based upon the use of specific, recently discovered wild strains of *Agaricus bisporus* which produce predominantly four-spored basidia. More importantly, the spores produced upon the basidia of these wild strains have been found to be homokaryotic, by virtue of their lack of fertility, their lack of heteroallelism and their ready ability to mate with other homokaryons.

Significantly, it has been found that the homokaryons of the wild four-spored strains of *Agaricus bisporus* will interbreed freely with both wild and cultivated two-spored strains of the same species using conventional crossbreeding techniques. Thus, hybrids combining the desirable genetic background of traditional breeding stocks of *Agaricus bisporus* with the gene or genes that confer the four-spored trait may be formed. When these hybrids are induced to produce mushrooms, following transfers to grain medium and compost medium, the hybrid mushrooms have basidia which predominantly bear three or more spores, most of which will be homokaryotic. Thus, a hybrid strain of *Agaricus bisporus* which carries the trait for the production of basidia which predominantly bear at least three spores can then be used in place of the wild predominantly four-spored strains to produce further descendants which also have the same or similar trait.

The percentage of hybrid homokaryotic offspring that will carry the gene or genes for the four-spored or two-spored traits will depend upon the number of genetic loci involved and upon whether the hybrid receives copies of the four-spored gene or genes from one or both parents. By selecting homokaryotic offspring of hybrids on the basis of whether they carry any four-spored gene or not, it is then possible to design and produce at will subsequent generations of hybrids which exhibit one of the three following behaviors: (i) four-spored hybrids whose direct descendants will all carry and express the four-spored trait, (ii) four-spored hybrids whose direct descendants will show segregation for two-spored and four-spored traits, and (iii) two-spored hybrids whose offspring carry only the two-spored trait. In this manner, through repeated backcrossing, using appropriate hybrid homokaryotic offspring, the gene or genes determining the four-spored trait can be incorporated independently within the genetic background of any traditional two-spored breeding stock.

A preferred technique to produce hybrid heterokaryons of *Agaricus bisporus* is to transfer inoculum of each of two substantially pure cultures of homokaryons to a suitable medium, for example, agar media such as potato dextrose agar (PDA) or complete yeast medium agar (CYMA). The inocula are placed about 1 to 2 centimeters apart. The colonies that grow from the inocula are allowed to grow until a junction zone of extensive contact along the opposing margins of the two colonies has occurred. Mating between sexually compatible homokaryons occurs via cell-fusion and the formation of common or shared cytoplasm. Fluffy or strandy mycelium is sometimes seen at this point in compatible crosses. Inoculum from the junction zone of successful crosses, which will contain novel hybrid heterokaryotic mycelium, is then transferred to a fresh medium to establish a heterokaryotic culture. On this latter culture, tests to confirm heterokaryosis, which indicates a successful cross, are subsequently performed. Heterokaryosis can be determined by genetic evaluation, demonstration of fertility or comparable methodologies.

Using the method of the present invention, the hybrids formed often show unusual vigor. By vigor, it is meant that the hybrids grow and fruit rapidly, and normal mushrooms are produced normally and abundantly. Moreover, the basidia of these hybrids are predominantly four-spored, indicating that the four-spored trait exhibits genetic dominance with substantial penetrance in the hybrids. It is noted, however, that, with regard to the expression of the trait, a substantial minority of three-spored basidia are often produced in certain hybrids. In fact, it appears possible that some hybrids bearing predominantly three-spored basidia might be encountered. Based on prior experience, two-thirds of the spores produced by these three-spored basidia are expected to be homokaryotic. Thus, the expression of a trait for the production of basidia which predominantly bear at least three spores is sufficient to produce predominantly homokaryotic spores. In addition, spores produced by the hybrids germinate rapidly and normally.

Because the basidia of the new hybrid are predominantly four-spored, most spores will produce homokaryotic offspring. Thus, homokaryons from the new hybrid, predominantly four-spored *Agaricus bisporus* may be used to interbreed with other strains of *Agaricus bisporus* to introduce the predominantly four-spored trait into the breeding stock of those strains.

More importantly, because the homokaryotic offspring greatly predominate, the necessity for genetic screening is eliminated. That is, high proportions of homokaryons on the order of from about 84 to about 99 percent, according to the model presented in Kerrigan and Ross, "Dynamic Aspects of Basidiospore Number in Agaricus," *Mycologia*, 79(2), 204–215 (1987), hereby incorporated by reference, are produced. The few heterokaryons present among spore offspring do not need to be screened out prior to using the homokaryotic offspring for breeding purposes. Once the four-spored trait has been included into breeding stock, it becomes easier to manipulate germ plasm for the production of hybrids improved with respect to various traits of economic importance, such as, mushroom color, size, yield, growth rate, temperature optima, disease resistance, and the like.

In order to demonstrate practice of the invention, germ plasm from wild four-spored *Agaricus bisporus*, designated JB2 and JB3, were used. These heterokaryotic stocks were each preserved as multiple-spore samples which were prepared from specimens collected from nature in Riverside County, California, in November, 1989 and December, 1990, respectively. A multi-spore culture, known as JB2-ms, is deposited with the American Type Culture Collection and is designated as ATCC 76072. These strains have a unique combination of genetic markers as reported in TABLE I set forth hereinbelow.

| Genotype data on stocks JB2 and JB3 of *Agaricus bisporus* from Riverside County, California, based on multi-spore cultures | | |
|---|---|---|
| Nuclear marker loci | JB2-ms Alleles | JB3-ms Alleles |
| P33N5 | 2/2 | 13/13* |
| P33N6 | 1/1 | 1/1 |
| P33N7 | 2/2 | —/— |
| P33N10/1 | 3/3 | 3/5 |
| P33N10/2 | 6/6 | 2/6 |
| P33N13 | 5/5 | 5/5 |
| P33N14 | 8/8 | 5/7 |
| P33N18 | 1/1 | 1/1 |
| P33N25 | 8/8* | 3/4 |
| P4N6 | 4/4 | 4/4 |
| P4N27 | 1/1 | 1/2 |
| GPT | 1/1 | —/— |
| ADH | 3/3 | 4/4 |
| PEP1 | 3/3 | 4/4 |
| PEP2 | 5/5 | 3/3 |
| BGLU | 3/5 | 5/5 |
| AAT | 3/3* | 1/1 |
| PGM | —/— | 2/2 |
| EST | 2/2 | 3/3 |
| MPI | S/F | S/S |

The uniqueness of these genotypes may be seen by comparison to the table of cultivar and wild *Agaricus bisporus* genotypes presented in Appendix 2 of Kerrigan et al., "The California Population of *Agaricus bisporus* Comprises At Least Two Ancestral Elements," *Systematic Botany*, 18:123–136 (1993), hereby incorporated by reference. An asterisk (*) denotes a novel allele not previously observed in an extensive global sample of *Agaricus bisporus* stocks.

Crosses were attempted as described hereinabove, between homokaryons from JB2 and known homokaryons from wild and cultivated, two-spored heterokaryotic breeding stocks of *Agaricus bisporus*.

In Experiment 1, individual homokaryons from JB2 were each crossed with a homokaryon from a commercial, nonhybrid, white, two-spored *Agaricus bisporus* stock belonging to the genotypic class No. 2 as set forth in Royse and May, "Use of Isozyme Variation to Identify Genotypic Classes of *Agaricus brunnescens*" *Mycologia* 74:93–102 (1982), which is hereby incorporated by reference and maintained in the Sylvan Spawn Laboratory Incorporated ("Sylvan Spawn") culture collection under the Stock 303 designation.

In Experiment 2, individual homokaryons from JB2 were each crossed with a homokaryon from a wild, heterokaryotic, two-spored, white *Agaricus bisporus* stock, belonging to the genotypic class No. 36, as identified in Kerrigan and Ross, "Allozymes for a Wild *Agaricus bisporus* Population: New Alleles, New Genotypes," *Mycologia* 81:433–443 (1989), hereby incorporated by reference. This strain of *Agaricus bisporus* is maintained in the Sylvan Spawn culture collection and is designated as Stock R.

In Experiment 3, individual homokaryons from JB2 and a different homokaryon taken from the same Stock R as employed in Experiment 2 were crossed.

In accordance with commerical practice, the novel hybrid heterokaryons formed from each cross were transferred to grain culture, and then, to compost culture to permit the production of hybrid mushrooms. Mushrooms have been produced in all crosses in all cases for which data is presently available. These mushrooms have predominantly four-spored basidia as reported in TABLE II hereinbelow. The proportions of four-spored and other basidia were determined by light microscopy as discussed in Kerrigan and Ross, "Dynamic Aspects of Basidiospore Number in Agaricus," *Mycologia*, 79(2), 204–215 (1987). Specifically, light microscopy was performed with a Nikon compound microscope with a 20× objective and 10× ocular. Lamellae were excised from the freshly harvested subject mushrooms and placed on a glass slide to form a "dry mount". Observations were made immediately by transmitted light. Basidia were sampled by selecting an area of the lamella at random, and most or all basidia at the appropriate developmental stage within that visual field were scored. Successive fields were scored until one hundred (100) basidia had been scored. This was repeated on two additional lamellae to furnish a total sample of three hundred (300) basidia from each hybrid mushroom. Basidia which had aborted spores or asynchronous spore development were excluded from scoring, as were basidia so mature that one or more spores might have been discharged prior to observation.

TABLE II

| Results of individual crosses between the four-spored stock JB2 and two two-spored stocks of *Agaricus bisporus* | | | | |
|---|---|---|---|---|
| JB2 homo-karyon No. | 5-spored | 4-spored | 3-spored | 2-spored |
| EXPERIMENT 1 - Stock JB2 crossed with homokaryon 3105 of Stock 303 | | | | |
| S8 | 0% | 78.7% | 21.3% | 0% |
| S9 | 0.03% | 69.0% | 30.0% | 0% |
| EXPERIMENT 2 - Stock JB2 crossed with homokaryon 9559 of Stock R | | | | |
| S3 | 0.03% | 59.4% | 38.3% | 2.0% |
| S9 | 0% | 68.0% | 29.0% | 3.0% |
| EXPERIMENT 3 - Stock JB2 crossed with homokaryon S5 of Stock R | | | | |
| S4 | 0% | 93.7% | 6.3% | 0% |
| S7 | 0% | 97.7% | 2.3% | 0% |
| S9 | 0% | 93.7% | 6.3% | 0% |

Thus, it should be clear that the method of the present invention provides basidia which are from about 59% to about 98% four-spored and from about 97% to 100% at least three-spored.

Initial results also indicate that many of these hybrids will fruit earlier and produce higher yields than a commercial hybrid, brown, two-spored strain which was used as a control. In addition, mushrooms having a white pileus coloration as well as mushrooms having a brown pileus coloration have been obtained. The white-capped trait is highly desired and valuable in the marketplace.

Based upon the foregoing disclosure, it should now be apparent that crossbreeding a four-spored *Agaricus bisporus* mushroom, the spores of which are homokaryotic, and a two-spored mushroom of the same species, as described herein will carry out the objects set forth hereinabove. Although the crossing of homokaryons is the preferred method of obtaining hybrids, it is also possible to cross a homokaryon with a heterokaryon or, in rare instances, to cross two heterokaryons. Thus, while homokaryons have been described throughout the specification, it should be understood that either homokaryons or heterokaryons, in any combination, may be employed. It is also possible to produce hybrids of *Agaricus bisporus* in less fully-defined situations in which mixtures of spores, protoplasts, or hyphal fragments are allowed to germinate or regenerate in mass cultures of uncertain ploidy, from which hybrid heterokaryons may subsequently be selected. It is, also, to be understood that any variations evident fall within the scope of the claimed invention and thus, the selection of specific crossbreeding techniques and sources of homokaryons or heterokaryons can be determined without departing from the spirit of the invention herein disclosed and described. Therefore, it is to be understood that other means of crossing, such as by genetic engineering, may also be employed for the present invention. Thus, the scope of the invention shall include all modifications and variations that may fall within the scope of the attached claims.

What is claimed is:

1. A method for the production of homokaryons from breeding stock of the mushroom *Agaricus bisporus* comprising the steps of: providing a first strain of *Agaricus bisporus* with tetrasporic parentage carrying at least one gene which determines the trait for production of mushrooms which produce basidia, among which basidia bearing at least three spores predominate; and crossing said first strain with at least a second strain of *Agaricus bisporus* to form at least one hybrid heterokaryotic culture, said at least one hybrid heterokaryotic culture being capable of producing mushrooms, the basidia of which predominantly bear at least three spores, most of said spores being homokaryotic.

2. A method, according to claim 1, wherein said second strain is of a stock that produces from one- to eight-spored basidia.

3. A method, according to claim 1, wherein said second strain is of a stock that is of wild origin.

4. A method, according to claim 1, wherein said second strain is of a stock that has been in cultivation.

5. A method, according to claim 1, wherein said second strain is of a stock that is of hybrid origin.

6. A method, according to claim 1, wherein said first strain is of a stock that is of wild origin.

7. A method, according to claim 1, wherein said first strain is of a stock that has been in cultivation.

8. A method, according to claim 1, wherein said first strain is of a stock that is of hybrid origin.

9. A method, according to claim 1, wherein said first and second strains are homokaryotic.

10. A method, according to claim 1, wherein said first and second strains are heterokaryotic.

11. A method, according to claim 1, wherein said first strain is homokaryotic and said second strain is heterokaryotic.

12. A method, according to claim 1, wherein said first strain is heterokaryotic and said second strain is homokaryotic.

13. A method for the production of homokaryotic spores, from basidia of the mushroom *Agaricus bisporus*, the basidia predominantly bearing at least three spores, comprising the steps of: providing a first *Agaricus bisporus* strain with tetrasporic parentage carrying at least one gene which determines the trait for production of mushrooms which produce basidia, among which basidia bearing at least three spores predominate; crossing a homokaryon from said first strain with a homokaryon from a second *Agaricus bisporus* strain to form at least one hybrid heterokaryotic culture; and managing said at least one hybrid heterokaryotic culture to produce the mushrooms having basidia which predominantly bear at least three spores.

14. A method, according to claim 13, wherein said step of crossing comprises the steps of: transferring inoculum of substantially pure cultures of homokaryons from each of said first and second strains of *Agaricus bisporus* to a suitable medium; permitting colonies of said inoculum to grow until said colonies contact and fuse with each other in a junction zone to form said at least one hybrid heterokaryotic culture; and transferring a portion of said at least one hybrid heterokaryotic culture to a fresh growth medium.

15. A method, according to claim 14, wherein said step of crossing further comprises the step of evaluating the resulting culture for heterokaryosis.

16. A method for introducing a trait for the production of mushrooms which produce basidia, among which basidia bearing at least three spores predominate, into breeding stock of the mushroom *Agaricus bisporus* comprising the steps of: providing a first strain of *Agaricus bisporus* with tetrasporic parentage carrying at least one gene which determines the trait for production of mushrooms which produce basidia, among which basidia bearing at least three spores predominate; and incorporating said at least one gene into the genetic background of at least a second strain of *Agaricus bisporus*, said second strain being bisporic, such that the new hybrid heterokaryotic breeding stock is capable of producing mushrooms that express the trait.

17. A method, according to claim 16, wherein said second strain is of a stock that produces one- to eight-spored basidia.

18. A method, according to claim 16, wherein said second strain is of a stock that is of wild origin.

19. A method, according to claim 16, wherein said second strain is of a stock that has been in cultivation.

20. A method, according to claim 16, wherein said second strain is of a stock that is of hybrid origin.

21. A method, according to claim 16, wherein said first strain is of a stock that is of wild origin.

22. A method, according to claim 16, wherein said first strain is of a stock that has been in cultivation.

23. A method, according to claim 16, wherein said first strain is of a stock that is of hybrid origin.

24. A method, according to claim 16, wherein said first and second strain are homokaryotic.

25. A method, according to claim 16, wherein said first and second strains are heterokaryotic.

26. A method, according to claim 16, wherein said first strain is homokaryotic and said second strain is heterokaryotic.

27. A method, according to claim 16, wherein said first strain is heterokaryotic and said second strain is homokaryotic.

28. A method for introducing a trait for the production of mushrooms which produce predominantly four-spored basidia into breeding stock of the mushroom *Agaricus bisporus* comprising the step of: providing a strain of *Agaricus bisporus* producing mushrooms having basidia which are predominantly four-spored; and incorporating from said *Agaricus bisporus* strain, at least one gene determining the trait for the production of mushrooms which produce basidia, among which basidia bearing four spores predominate, into the genetic background of an *Agaricus bisporus* strain producing mushrooms having predominantly two-spored basidia.

29. A method, according to claim 28, wherein said step of incorporating comprises the steps of: transferring inoculum of substantially pure cultures of homokaryons from each of said four-spored and two-spored strains of *Agaricus bisporus* to a suitable medium; permitting colonies of said inoculum to grow until said colonies contact and fuse with each other in a junction zone to form at least one hybrid heterokaryotic culture; and transferring a portion of said at least one hybrid heterokaryotic culture to a fresh growth medium.

30. A method, according to claim 29, wherein the step of incorporating further comprises the step of evaluating the resulting culture for heterokaryosis.

31. Homokaryons carrying at least one gene which determines the trait for the production of mushrooms which produce basidia, among which basidia bearing at least three spores predominate, produced from homokaryotic basidiospores on hybrid mushrooms, said hybrid mushrooms formed by providing a first strain of *Agaricus bisporus* with tetrasporic parentage carrying at least one gene which determines the trait for production of mushrooms which produce basidia, among which basidia bearing at least three spores predominate; and crossing said first strain with at least a second strain of *Agaricus bisporus* to form at least one hybrid heterokaryotic culture; said at least one hybrid heterokaryotic culture being capable of producing said hybrid mushrooms and their homokaryotic descendants which carry said at least one gene.

32. Homokaryons, according to claim 31, wherein said second strain is of a stock that produces one- to eight-spored basidia.

33. Homokaryons, according to claim 31, wherein said second strain is of a stock that is of wild origin.

34. Homokaryons, according to claim 31, wherein said second strain is of a stock that has been in cultivation.

35. Homokaryons, according to claim 31, wherein said second strain is of a stock that is of hybrid origin.

36. Homokaryons, according to claim 31, wherein said first strain is of a stock that is of wild origin.

37. Homokaryons, according to claim 31, wherein said first strain is of a stock that has been in cultivation.

38. Homokaryons, according to claim 31, wherein said first strain is of a stock that is of hybrid origin.

39. Homokaryons, according to claim 31, wherein said first and second strains are homokaryotic.

40. Homokaryons, according to claim 31, wherein said first and second strains are heterokaryotic.

41. Homokaryons, according to claim 31, wherein said first strain is homokaryotic. and said second strain is heterokaryotic 42. Homokaryons, according to claim 31, wherein said first strain is heterokaryotic and said second strain is homokaryotic.

43. A method for the production of vigorous hybrid strains of *Agaricus bisporus* comprising the step of combining genetic material originating from a strain of *Agaricus bisporus* with tetrasporic parentage carrying at least one gene which determines the trait for production of mushrooms which produce basidia, among which basidia bearing at least three spores predominate with genetic material from at least a second *Agaricus bisporus* strain.

44. A method, according to claim 43, wherein the vigorous hybrid strains of *Agaricus bisporus* produce mushrooms having a white pileus coloration.

45. A method, according to claim 43, wherein the vigorous hybrid strains of *Agaricus bisporus* produce mushrooms having a brown pileus coloration.

46. Heterokaryons carrying at least one gene which determines the trait for the production of mushrooms which produce basidia, among which basidia bearing at least three spores predominate, produced from a cross of homokaryons, at least one of said homokaryons being produced from a strain of *Agaricus bisporus* carrying at least one gene which determines the dominant trait for production of mushrooms which produce basidia, among which basidia bearing at least three spores predominate.

* * * * *